United States Patent
White

(10) Patent No.: US 7,195,605 B1
(45) Date of Patent: Mar. 27, 2007

(54) SIMPLE DYNAMIC ORTHOSIS

(76) Inventor: Christopher H. White, 33 Queen Ave. South, Minneapolis, MN (US) 55405

( * ) Notice: Subject to any disclaimer, the term of this patent is extended or adjusted under 35 U.S.C. 154(b) by 376 days.

(21) Appl. No.: 10/162,980

(22) Filed: Jun. 3, 2002

(51) Int. Cl.
*A61F 5/00* (2006.01)

(52) U.S. Cl. .............................. 602/21; 602/64; 602/57

(58) Field of Classification Search ............ 602/60–65, 602/19–22, 57–59, 5, 1, 903, 75–78, 41, 602/52, 54, 42–47
See application file for complete search history.

(56) References Cited

U.S. PATENT DOCUMENTS

| | | | | |
|---|---|---|---|---|
| 2,280,506 A | * | 4/1942 | Betts | 128/894 |
| 2,484,130 A | * | 10/1949 | Thibault | 602/62 |
| 2,875,758 A | | 3/1959 | Fuzak et al. | 128/157 |
| 3,050,053 A | * | 8/1962 | Peckham | 602/5 |
| 3,062,546 A | * | 11/1962 | Horton et al. | 473/61 |
| 3,245,406 A | * | 4/1966 | Chardack | 602/79 |
| 3,312,219 A | * | 4/1967 | Peckham | 602/65 |
| 3,411,159 A | * | 11/1968 | Berkhemer | 2/159 |
| 3,606,343 A | * | 9/1971 | Lemon | 473/62 |
| 3,790,168 A | * | 2/1974 | Hashimoto | 473/62 |
| 3,880,159 A | | 4/1975 | Diamond | 128/157 |
| 3,888,247 A | | 6/1975 | Stenvall | 128/155 |
| 3,896,498 A | * | 7/1975 | Pang | 2/20 |
| 3,971,374 A | * | 7/1976 | Wagner | 602/58 |
| 3,989,041 A | * | 11/1976 | Davies | 602/62 |
| 4,176,839 A | * | 12/1979 | Pinkus | 602/64 |
| 4,345,590 A | * | 8/1982 | Nakajima | 602/65 |
| 4,366,814 A | | 1/1983 | Riedel | 128/156 |
| 4,479,648 A | * | 10/1984 | Alivo, Jr. | 473/62 |
| 4,519,097 A | * | 5/1985 | Chappell et al. | 2/16 |
| 4,549,537 A | | 10/1985 | Ender | 128/87 A |
| 4,854,310 A | * | 8/1989 | Lee | 602/21 |
| 4,875,476 A | * | 10/1989 | Garcia | 602/65 |
| 4,966,137 A | | 10/1990 | Davini | 128/87 R |
| 5,107,826 A | * | 4/1992 | Andersson | 602/19 |
| 5,116,675 A | * | 5/1992 | Nash-Morgan | 428/343 |
| 5,154,690 A | * | 10/1992 | Shiono | 602/5 |
| 5,160,314 A | | 11/1992 | Peters | 602/21 |
| 5,197,149 A | * | 3/1993 | Overton | 2/162 |
| 5,267,952 A | | 12/1993 | Gardner | 602/58 |
| 5,306,229 A | | 4/1994 | Brandt et al. | 602/26 |
| 5,338,290 A | | 8/1994 | Aboud | 602/75 |
| 5,350,418 A | * | 9/1994 | Janevski et al. | 607/111 |
| 5,376,066 A | * | 12/1994 | Phillips et al. | 602/21 |
| 5,409,451 A | * | 4/1995 | Daneman | 602/21 |
| 5,413,553 A | * | 5/1995 | Downes | 602/21 |
| 5,466,215 A | * | 11/1995 | Lair et al. | 602/21 |
| 5,478,306 A | | 12/1995 | Stoner | 602/20 |
| 5,662,594 A | | 9/1997 | Rosenblatt | 602/16 |
| 5,681,268 A | | 10/1997 | Radman | 602/20 |

(Continued)

*Primary Examiner*—Danton D. DeMille
*Assistant Examiner*—Huong Q. Pham
(74) *Attorney, Agent, or Firm*—Z. Peter Sawicki; Westman, Chaplin & Kelly, P.A.

(57) ABSTRACT

The present invention includes an adhesive bandage for use in one or more disorders of a joint and/or associated appendage. The method of the present invention includes placing a user's joint in a corrective orthopedic position, and adhering an adhesive bandage onto an external surface of the user's joint, such that the adhesive bandage stimulates a somatic reflex arc when the user's joint deviates from the corrective orthopedic position to prompt the user to return the joint to the corrective orthopedic position.

3 Claims, 10 Drawing Sheets

U.S. PATENT DOCUMENTS

| | | | |
|---|---|---|---|
| 5,711,312 A * | 1/1998 | Staudinger | 128/845 |
| 5,769,804 A | 6/1998 | Harris et al. | 602/21 |
| 5,792,091 A * | 8/1998 | Staudinger | 602/57 |
| 5,802,614 A * | 9/1998 | Melone, Jr. | 2/161.1 |
| 5,843,025 A * | 12/1998 | Shaari | 602/53 |
| 5,865,783 A | 2/1999 | Klimoski | 602/64 |
| 5,921,949 A | 7/1999 | Dray | 602/64 |
| 5,925,007 A | 7/1999 | Ashline | 602/21 |
| 6,106,492 A | 8/2000 | Darcey | 602/8 |
| 6,120,471 A | 9/2000 | Varn | 602/21 |
| 6,126,625 A | 10/2000 | Lundberg | 602/27 |
| 6,191,337 B1 * | 2/2001 | Himmelsbach | 602/54 |
| 6,200,286 B1 | 3/2001 | Zamani | 602/64 |
| 6,217,536 B1 | 4/2001 | Gustafson | 602/21 |
| 6,248,932 B1 * | 6/2001 | Himmelsbach | 602/41 |
| 6,293,919 B1 | 9/2001 | Manente | 602/21 |
| 6,315,748 B1 * | 11/2001 | Morgan, Jr. | 602/21 |
| 6,367,081 B1 * | 4/2002 | Harris | 2/16 |
| 6,399,852 B1 * | 6/2002 | Barron | 602/41 |
| 6,491,653 B1 * | 12/2002 | Hamill | 602/5 |
| 6,769,428 B2 * | 8/2004 | Cronk et al. | 128/200.24 |
| 6,849,056 B1 * | 2/2005 | Wiggins et al. | 602/21 |
| 2002/0091348 A1 * | 7/2002 | Joseph | |

* cited by examiner

SIMPLE DYNAMIC ORTHOSIS

CROSS-REFERENCE TO RELATED APPLICATION(S)

None.

BACKGROUND OF THE INVENTION

The present invention generally relates to an apparatus and a method of treating one or more disorders of a joint and/or an associated appendage of a patient. More specifically, the present invention relates to an adhesive bandage and a method of using the adhesive bandage to prevent, treat or correct one or more disorders of the joint and/or the associated appendage of the patient.

Rehabilitation of injury and pain to a joint as a result of trauma, repetitive use or improper posture typically requires correct positioning of a joint, an associated appendage and/or a surrounding injured region. Correct positioning of the joint typically involves maintenance of the joint, the associated appendage and/or surrounding injured region in a corrective orthopedic and/or least distressed joint position that is effective to promote recovery. Unfortunately, correct positioning of the joint to facilitate the recovery process is not typically maintained by a patient for a sufficient period of time. Consequently, orthotics have been developed to facilitate the rehabilitation process. Orthotics may be characterized as a method of treatment that assists in maintenance of the correct orthopedic position for a joint, associated appendage, and/or injured region undergoing rehabilitation.

The most common disorders of the joints and/or associated appendages include carpal tunnel syndrome, plantar fascitis, neck pain and back pain. Numerous strategies have been proposed to prevent or treat injured, painful or swollen joints, appendages and/or surrounding injured regions. Prevention efforts have consisted of modification of work, home or avocational activities (ergonomics). Treatment may include permitting the joint, associated appendage and/or injured region to heal by reducing swelling of the joint, for example. Currently, the most widely accepted route to reduce swelling is to restrict movement of the joint and/or associated appendage through the use of non-surgical or conservative treatments like splints, bandages and/or local steroid injection.

As an example, one or more splints may be used to immobilize a wrist in treatment of carpal tunnel syndrome treatment. The splint is typically a fixed and/or rigid member that is applied to the volar or dorsal surface of a hand and secured circumferentially to the hand or a forearm. The splint may be used during working when repetitive use of the fingers and hand may occur, and/or at night when natural resting patterns like the fetal posture draw the hands into a flexed, supinated and/or radially deviated position.

The splint is designed to maintain the wrist in the corrective orthopedic and/or least distressed position while restricting movement of the wrist. Thus, the splint is believed to minimize pressure in the carpal tunnel of the wrist. Minimizing most, if not all, pressure in the carpal tunnel is believed to reduce compression of the median nerve, and therefore, eliminate carpal tunnel syndrome.

Unfortunately, splints are not effective for several reasons. For example, splints are cumbersome and awkward in the work environment as well as cosmetically displeasing. Splints also limit a person's mobility for work or other activities. In addition, user's wearing the splint often report that the joint moves out of the splinted corrective orthopedic and/or least distressed position during use of the associated hand. Night users often complain that splints are uncomfortable and interfere with intimacy. Each factor reduces the efficacy of splints and more importantly, decreases wear compliance.

Furthermore, the use of the splint and/or device to immobilize the joint is generally an expensive method of treatment as the splint or device often requires careful customization to match a person's body. Steroid injection is another method of treatment, but, due to the potential danger of chemical neuritis or aseptic necrosis, steroid injection is often limited to three or four administrations.

The use of ice, massage, acupuncture and electromodalities have also been employed. When such conservative treatments are not effective, surgery is typically recommended. However, surgery is not always effective and can also lead to post-surgical problems, such as reflex dystrophy. Additionally, only 23% of all Carpal Tunnel Syndrome patients were able to return to their previous professions following surgery. Furthermore, surgery is a costly and irreversible method of treatment. Therefore, there exists a need for an apparatus which maintains a correct orthopedic position of a joint undergoing rehabilitation. In addition, there exists a need for a method of treating a disorder to a joint that permits full range of motion of the joint without compromising joint function. Furthermore, there exists a need for efficiently treating joint disorders while minimizing the use of expensive and/or permanent methods of treatment, such as drugs or surgery.

BRIEF SUMMARY OF THE INVENTION

The present invention includes an adhesive bandage for use in one or more disorders of a joint and/or associated appendage. The method of the present invention includes placing a user's joint in a corrective orthopedic position, and adhering an adhesive bandage onto an external surface of the user's joint, such that the adhesive bandage stimulates a somatic reflex arc when the user's joint deviates from the corrective orthopedic position to prompt the user to return the joint to the corrective orthopedic position.

DETAILED DESCRIPTION

The present invention generally relates to an apparatus and a method of treating one or more disorders of a joint and/or any associated appendage of a patient. More specifically, the present invention relates to an adhesive bandage and a method of using the adhesive bandage to support, align, prevent, treat and/or correct one or more disorders of the joint and/or associated appendage of the patient.

Figure 1:
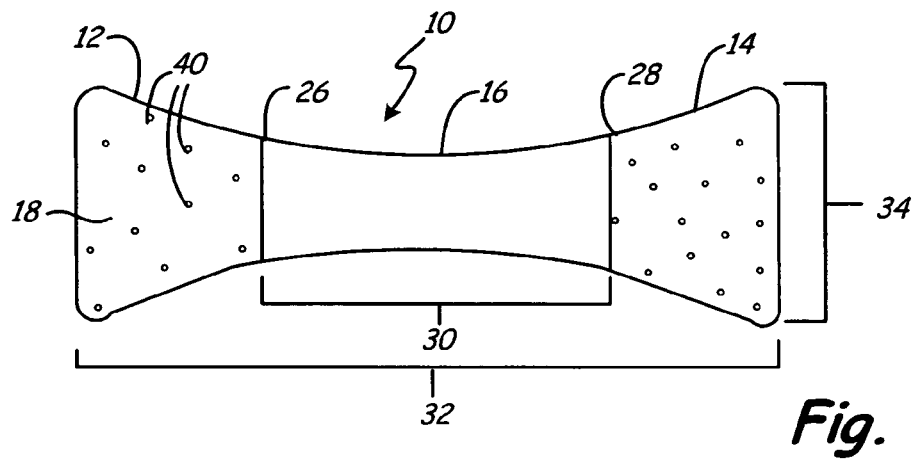
FIG. 1 is a top plan view of an adhesive bandage used in accordance with the present invention.

One form of the adhesive bandage of the present invention is generally depicted at 10 in FIG. 1. As used herein, the term "adhesive bandage" may also be referred to as a "simple dynamic orthosis" or "SDO". Therefore, the terms "adhesive bandage" and "simple dynamic orthosis' or "SDO" may be used interchangeably throughout the specification.

Figure 2:
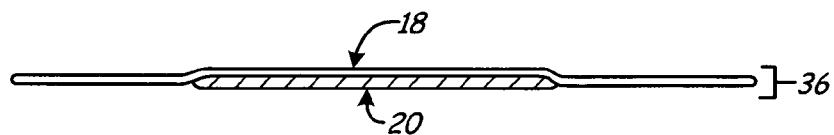
FIG. 2 is a side plan view of the adhesive bandage depicted in FIG. 1.
Figure 3:
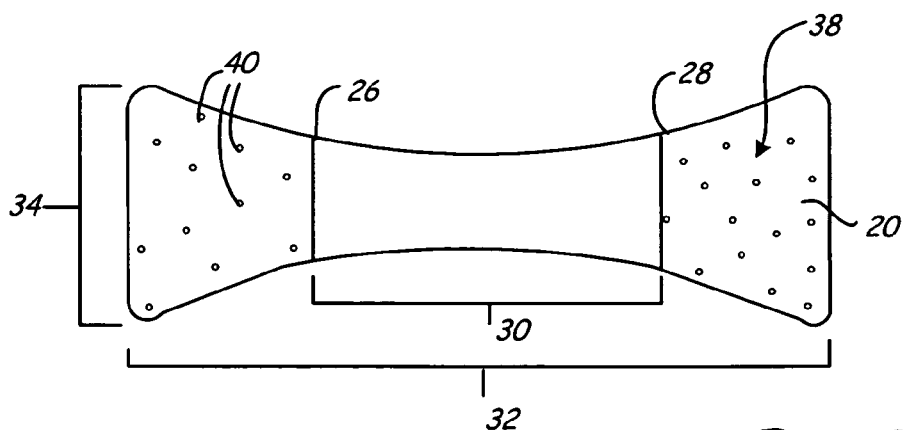
FIG. 3 is a bottom plan view of the adhesive bandage depicted in FIG. 1.

The adhesive bandage 10 that may be worn by a user (not shown) generally includes an elongated strip that terminates at proximal end 12 and distal end 14. The adhesive bandage also has center 16 that is located between ends 12 and 14. As best depicted in FIGS. 2 and 3, the adhesive bandage 10 includes an outer or top surface or layer 18 and an inner or bottom surface or layer 20. The top surface 18 is generally exposed to air while the bottom surface 20 is adapted to be worn next to a dorsal cutaneous surface 22 of a user's body (not shown) as best illustrated in FIGS. 1–3, and 5–12. As used herein, the term "dorsal cutaneous surface 22" may also be used to refer to as a "user's skin 22" when practicing the present invention. Accordingly, the terms "dorsal cutaneous surface 22" or "user's skin 22" may be used interchangeably throughout the specification.

Proximal end 12 and distal end 14, although generally depicted herein as curvilinear, may be any shape, such as linear or winged, so long as ends 12 and 14 are capable of conforming to the surface 22 of the user's body. The adhesive bandage 10 has a pair of longitudinally spaced transverse stretch zones 26 and 28. In use, the stretch zones 26 and 28 help adjust a longitudinal length 30 of the center 16 when the adhesive bandage 10 is used in accordance with the present invention. As a result, stretch zones 26 and 28 are also effective in adjusting a longitudinal length 32 of the adhesive bandage 10 to more fully conform to the user's body. Although the present invention generally depicts stretch zones 26 and 28, it is to be understood that the adhesive bandage 10 may have more than or less than two stretch zones in order to provide the required degree of stretch in the adhesive bandage 10.

The adhesive bandage 10 may span any length, as indicated by 32 in FIGS. 1 and 3. Typically, the length 32 will span a distance on a treated area of the user's body that is capable of stimulating one or more cutaneous sensory nerves (not shown) located in the user's body to induce a somatic sensation reflex arc in the user. Preferably, the length 32 of the bandage 10 is effective to stimulate one or more cutaneous sensory nerves located underneath the adhesive bandage 10 that is attached to the user's body at the proximal end 12 and distal end 14 to induce the somatic sensation reflex arc that communicates pain to the user.

The adhesive bandage 10 may generally have a lateral width 34. Typically, the width 34 will vary depending upon the surface and/or dimensions of the treated area of the user's body. In addition, the width 34 is typically wide enough to treat only the necessary area on the user's body requiring treatment, while a remainder portion of the user's body remains unfettered.

The adhesive bandage 10 may have any thickness, as indicated by 36 in FIG. 2. Typically, the thickness 36 of the adhesive bandage 10 will vary depending on the surface 22 and/or dimensions of the user's body when practicing the present invention. As an example, the thickness 36 may range from about 3 mils (about 0.07 millimeters (mm)) thick to about 20 mils (about 0.5 mm) thick when practicing the present invention, though thicknesses outside of this range are permissible. Preferably, the thickness 36 ranges from about 5 mils to about 10 mils to eliminate any discomfort associated with use of the adhesive bandage 10.

The adhesive bandage 10 typically includes an adhesive 38 to adhere the adhesive bandage 10 onto the user's body. The adhesive 38 may be coated onto an entire length 32 of the inner surface 20 of the adhesive bandage 10, or onto ends 12 and 14. Preferably, the adhesive 38 is placed onto the inner surface 20 of ends 12 and 14 of the adhesive bandage while the center 16 remains free of the adhesive 38. In general, any adhesive, such as an acrylate adhesive or a urethane foam adhesive may be used as the adhesive 38 when practicing the present invention.

The adhesive 38 at ends 12 and 14 that is in contact with the inner surface 20 of the adhesive bandage 10 serves several important purposes. First, the adhesive 38 at ends 12 and 14 secures the adhesive bandage 10 onto the cutaneous surface 22 of the user's body. Consequently, the adhesive 38 helps to keep the adhesive bandage 10 in close proximity to, and preferably in contact with, the user's body.

Secondly, the adhesive 38 maintains the adhesive bandage 10 in fixed relation with one or more attachment sites located on the user's body through the proximal end 12 and the distal end 14 to prevent any portions of the adhesive bandage 10 from shifting or sliding relative to the attachment sites. The attachment sites are typically located over a distance that encompasses a joint requiring corrective treatment and/or corrective positioning. Preferably, the attachment sites are located at one or more cutaneous sensory nerves that send pain signals when stimulated.

Still more preferably, the attachment sites for the adhesive bandage 10 are located across two or more different bones that are capable of bridging the joint requiring corrective treatment and/or corrective positioning, and over one or more cutaneous sensory nerves that send pain signals to the user when stimulated. Furthermore, by virtue of maintaining the adhesive bandage 10 in the desired location on the user's body, the adhesive bandage 10 permits independent movement of other areas of the user's body that are not attached to, nor covered by the adhesive bandage 10.

In addition, the adhesive 38 at ends 12 and 14 preferably prevent delamination of the adhesive bandage 10 from the dorsal surface 22 of the user's body. Furthermore, by maintaining the adhesive bandage 10 in contact with the dorsal surface 22 of the user's body, the adhesive 38 promotes stimulation of the cutaneous sensory nerves (not shown) when the adhesive bandage 10 is stretched. Indeed, the adhesive 38 that adheres the adhesive bandage 10 onto the dorsal surface 22 facilitates induction of the somatic reflex arc that is required to transmit pain signals to the user, and thereby prompt the user to eliminate the pain by removing the stretch on the adhesive bandage 10.

The adhesive bandage 10 may be characterized as a lightweight flexible apparatus that promotes ease of wear. In addition, the adhesive bandage 10 may be prepared from a porous stretchable material that allows the dorsal surface 22 to breathe while it is being worn. Preferably, the adhesive bandage 10 is manufactured from an elasticized material to conform to the particular dorsal surfaces 22 of the user's body while allowing the underlying skin 22 to breathe and move.

Although the adhesive bandage 10 should preferably exhibit a degree of elasticity to permit conformance to the user's body, the elasticity should also be balanced by a degree of resiliency such that the adhesive bandage 10 returns to its original size and shape when the stretching force is removed. Some non-exhaustive examples of materials that may be used to form the adhesive bandage 10 include any natural fiber or film, such as fibers and/or films derived from cellulosic materials, or the like, any synthetic fiber or film, such as films of polyurethane, vinyl, ethylene vinyl acetate, acetate, polyethylene, polyester, nylon; elastomers, such as natural rubber, neoprene rubber, or the like; elasticized fibers, such as those sold under the trademark name Lycra™, any non-woven materials that include dacron, rayon, and mixtures thereof. In addition, the adhesive bandage may be sterile or non-sterile. Preferably, the adhesive bandage 10 is non-sterile when practicing the present invention.

The adhesive bandage 10 may have a plurality of pores, holes, or spaces 40 that extend partially or fully through the adhesive bandage 10. Preferably, the plurality of pores, holes or spaces 40 extend through the entire thickness 36 of the adhesive bandage 10. These pores, spaces, or holes 40 permit adequate supply of air to the user's body while enabling moisture to be removed away from the user's skin 22 to promote good skin integrity. In addition, the pores, spaces or holes 40 ensure dryness that provides a comfortable feel against the user's skin 22. The pores, spaces or holes 40 may also help minimize heat buildup during manual activities that involve the user's body.

Figure 4:
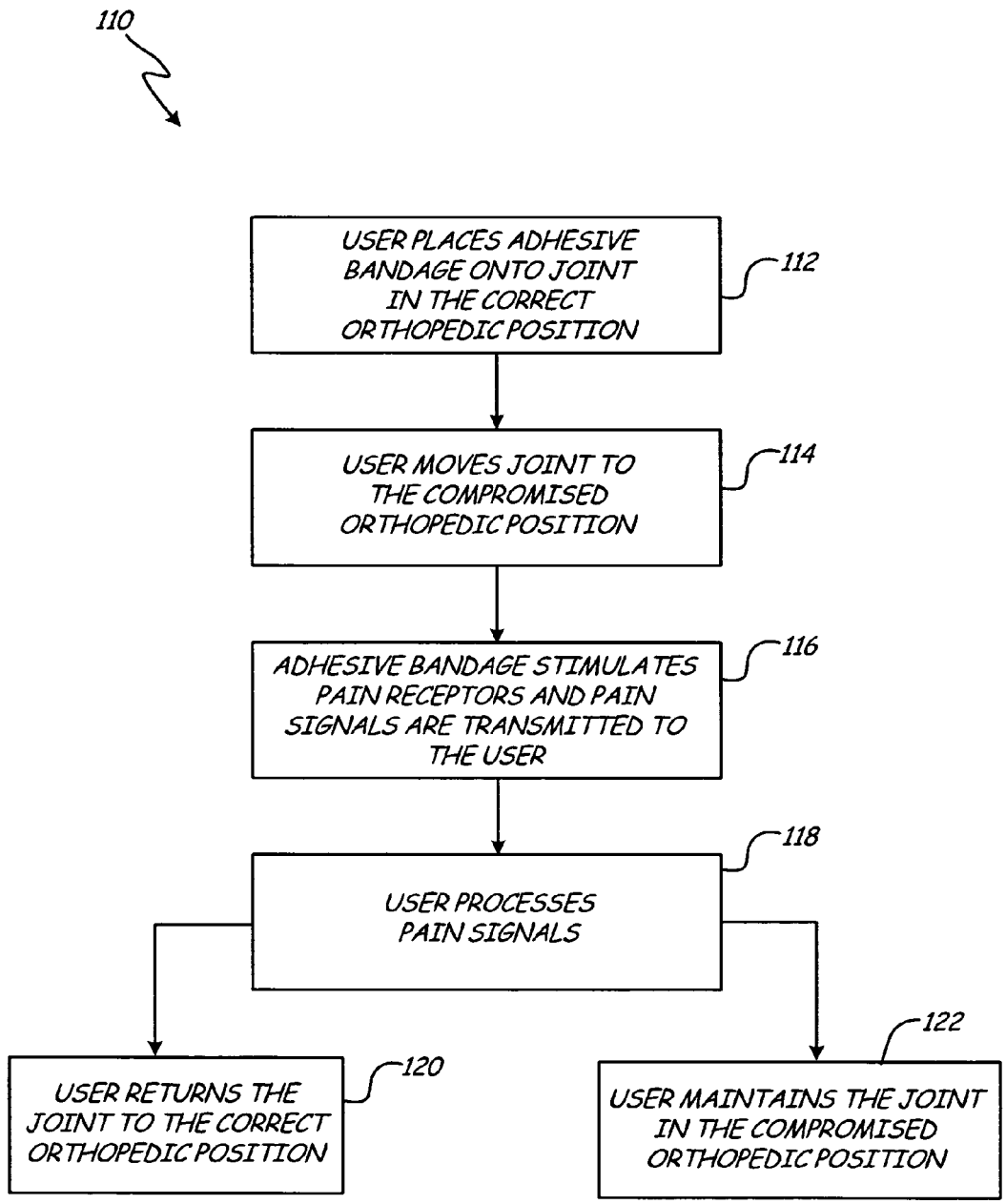
FIG. 4 is a flow diagram of a preferred method of stimulating a somatic reflex arc that prompts a user to maintain a correct orthopedic position of a joint.

A preferred method of using the adhesive bandage 10 is generally depicted at 110 in FIG. 4. In the method 110, the adhesive bandage 10 is placed onto the user's joint (not shown), such as a wrist, an ankle, a neck or the like when the user's joint is in slight extension or least distressed joint position at step 112. The slight extension or least distressed joint position is the corrective orthopedic position for the joint. At step 114, the user moves the joint away from the slight extension and/or least distressed joint position and the joint is placed in a compromised orthopedic position. At step 116, the adhesive bandage stimulates one or more cutaneous sensory nerves located on the dorsal surface of the user's body beneath the adhesive bandage. Stimulating the cutaneous sensory nerves stimulates the somatic reflex arc located in the user's body. At step 118, one or more pain signals from the cutaneous sensory nerve are sent to the user's central nervous system for processing through one or more afferent pain neuroreceptors (nociceptors). The user must also decide to (1) return the joint to the corrective orthopedic position to reduce and/or eliminate the pain or (2) maintain the joint in the compromised orthopedic position that further stimulates the somatic reflex arc at step 118.

At step 120 the user chooses to return the joint to the corrective orthopedic position, and the pain transmitted to the user is reduced and/or eliminated. At step 122, the user chooses to maintain the joint in the compromised orthopedic position, and pain signals are transmitted to the user until the joint is returned to the corrective orthopedic position.

Figure 5:
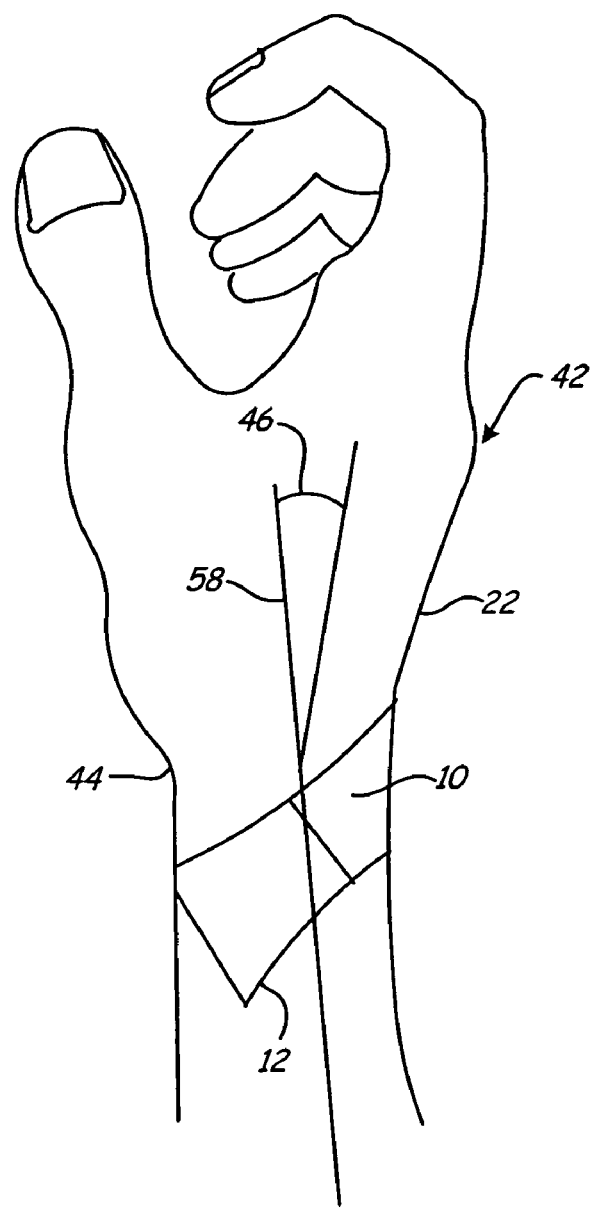
FIG. 5 is a lateral view of the adhesive bandage of the present invention applied to a user's wrist that is placed in a correct orthopedic position.
Figure 6:
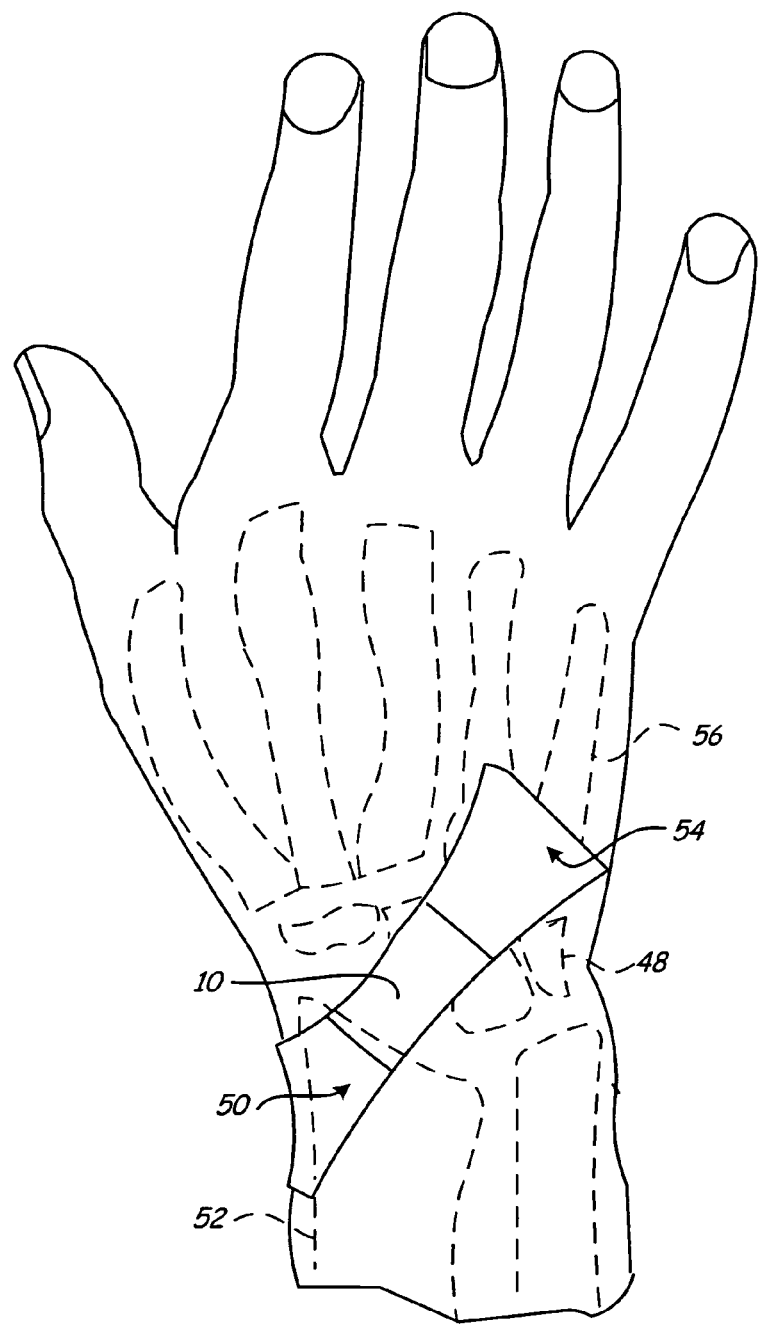
FIG. 6 is a dorsal view of the adhesive bandage of the present invention applied to the user's wrist of FIG. 5.

As an example, the adhesive bandage 10 may be used to treat carpal tunnel syndrome as best depicted in FIGS. 5–6. When the adhesive bandage 10 is used to treat carpal tunnel syndrome, the adhesive bandage 10 is placed onto the dorsal cutaneous surface 22 of a user's hand 42 when a wrist 44 of the user's hand 42 is in the corrective orthopedic position. The corrective orthopedic position refers to when a wrist is placed in a slightly extended position, such as when the wrist 44 is extended by angle alpha 58 or less, as best illustrated in FIG. 5. When the user's wrist 44 is in the corrective orthopedic position, the wrist 44 or carpal bones 48 that include the carpal tunnel and flexor tendons (not shown) of the user's hand 42 do not constrict the carpal tunnel. Furthermore, when the user's wrist 44 is in the corrective orthopedic position, the flexor tendons within the carpal tunnel reduce compression of the median nerve that is also located in the carpal tunnel.

After placing the adhesive bandage 10 onto the user's hand 42 when the wrist 44 is in the corrective orthopedic position, the proximal end 12 of the adhesive bandage 10 may be adhered to, or affixed over a lateral end 50 of a radius bone 52 while the distal end 14 of the adhesive bandage 10 may be adhered to, or affixed over a base 54 of a $5^{th}$ metacarpal 56. The adhesive bandage 10 that is used to treat carpal tunnel syndrome is preferably long enough to span a diagonal length between the lateral end 50 of the radius bone 52 and the base 54 of the $5^{th}$ metacarpal 56. Preferably, the proximal end 12 of the adhesive bandage 10 is adhered diagonally to the user's hand 42 at a location slightly beyond the lateral end 50 of the radius bone 52 while the distal end 14 of the adhesive bandage 10 is adhered diagonally at a location slightly beyond the base 54 of the $5^{th}$ metacarpal 56.

When the user's wrist 44 deviates from the slightly extended position, a cutaneous nerve (not shown) in the user's hand 42 is stimulated, and one or more pain signal(s) are communicated to the user. For example, when the wrist 44 moves into a flexion, flexion/supination or flexion/supination/radial position, the flexion, flexion/supination or flexion/supination/radial position causes the adhesive bandage 10 to stretch. Cutaneous sensory nerves (not shown) that are located in the user's hand 42 are stimulated or activated by the stretch, and pain signals are transmitted to the Central Nervous System of the user through afferent pain neuroreceptors (nociceptors). After transmission, the pain signals are integrated in the Central Nervous System and subsequently communicated to the user. Stimulation of the cutaneous sensory nerves with transmission of pain signals through the Central Nervous System to the user induces the somatic sensation reflex arc located in the user's hand 42. As used herein, the term "somatic sensation reflex arc" refers to a stimulus-response sequence that occurs after stimulation of one or more cutaneous pain neuroreceptors (nociceptors) that may be located under a cutaneous surface of a user's body.

After the pain signals are received by the user, the user must make a decision to respond to the pain signals by (1) continuing to maintain the wrist in the flexion, flexion/supination or flexion/supination/radial position or (2) eliminating the pain and returning the wrist 44 to the corrective orthopedic position. Therefore, the adhesive bandage 10 dynamically maintains the corrective orthopedic position of the wrist 44 or carpal bones 48 by providing an immediate cutaneous stimulus to the user any time the wrist 44 or carpal bones 48 deviates from the corrective orthopedic position.

In addition, the adhesive bandage 10 is a dynamic method of treatment that still permits full range of motion of the wrist 44 without compromising wrist 44 function. Thus, the dynamic quality of the adhesive bandage 10 enables the user to perform work activities or maintain natural resting positions or fetal posture of the wrist 44 for brief periods of time, while subsequent and continuous cutaneous stimulation reminds the user to return the wrist 44 to the corrective orthopedic position.

Little, if any, pressure to the median nerve generally occurs when the user's wrist 44 is in the corrective orthopedic position. Eliminating most, if not all, pressure to the median nerve helps to eliminate carpal tunnel syndrome that plagues people as a result of constriction or compression of the median nerve that occurs when the wrist is in the flexed position.

The adhesive bandage 10 provides a unique method of restricting movement of the wrist 44 or carpal bones 48 by stimulating cutaneous sensory nerves of the user's hand 42 located under the adhesive bandage 10 that signal the user to keep the wrist 44 in the corrective orthopedic or least distressed wrist position. Furthermore, the adhesive bandage 10 provides a means for reminding the user to retain the wrist 44 in the corrective orthopedic position so that most, if not all pressure on the median nerve may be eliminated during various manual activities as a result of flexing the wrist 44.

The adhesive bandage 10 of the present invention provides an innovative approach to the conservative treatment of carpal tunnel syndrome. Additionally, using the adhesive bandage 10 to treat carpal tunnel syndrome in accordance with the present invention eliminates cumbersome and awkward use of other devices and/or apparatuses that may be used to treat this syndrome, and permits unrestricted use of the user's hand 42. Furthermore, the adhesive bandage 10 does not compromise the cosmetic appearance of the user's hand 42 while undergoing treatment for carpal tunnel syndrome. In a second embodiment, the adhesive bandage 10 may be used to treat plantar fascitis. As used herein, the term "plantar fascitis" refers to an inflammation of fasciae located on a plantar sole of a foot. Plantar fascitis may occur when the fasciae becomes inflamed as a result of trauma, injury or repetitive movement of the foot.

Figure 7:
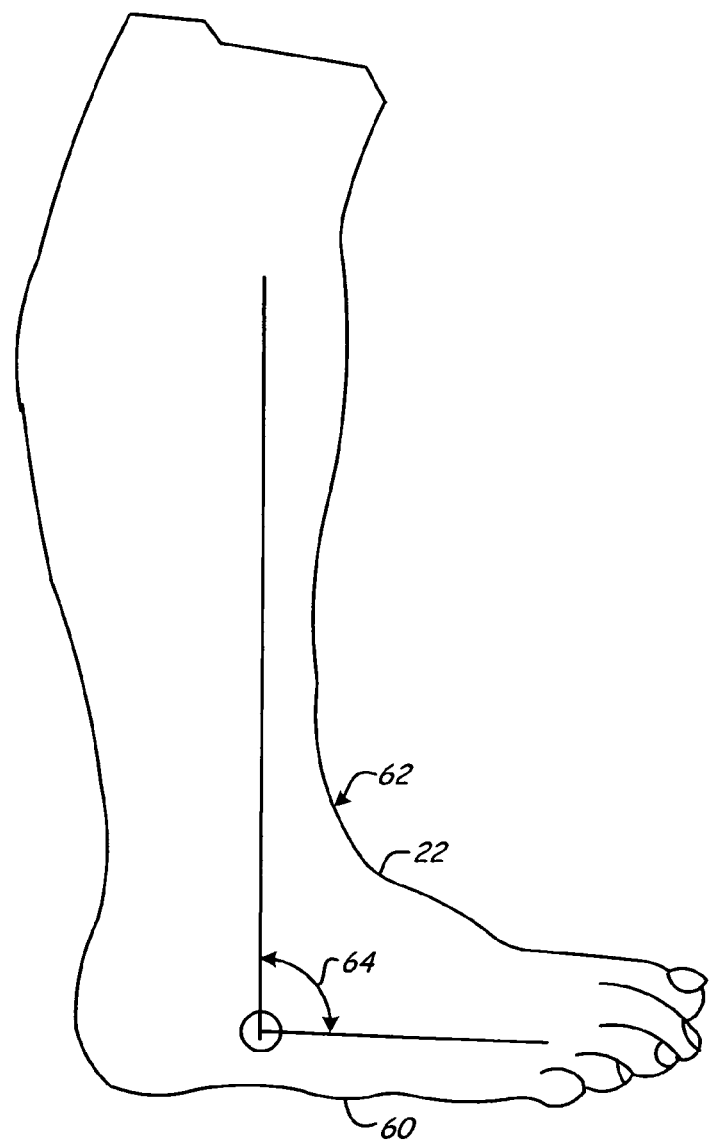
FIG. 7 is a lateral view of a user's foot that is placed in a correct orthopedic position.
Figure 8:
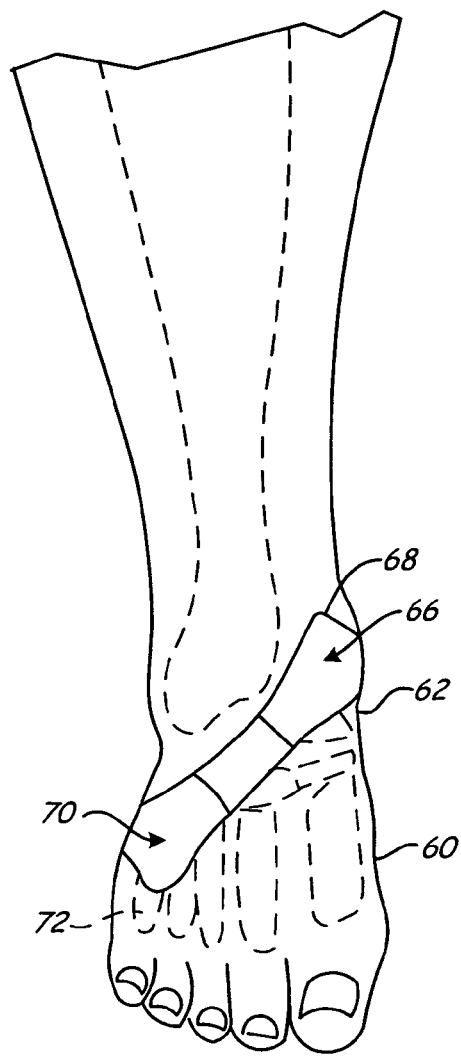
FIG. 8 is a dorsal view of the adhesive bandage of the present invention applied to the user's foot depicted in FIG. 7.

When treating plantar fascitis, the bandage 10 is typically placed onto the dorsal cutaneous surface 22 of a user's foot 60 when an ankle 62 of the user is in a slight dorsiflexion position, as best illustrated in FIG. 7 and measured by angle beta 64. As used herein, the term "dorsiflexion" refers to an upward turn of the ankle, as best illustrated in FIG. 7. Placing the ankle 62 in the slight dorsiflexion position places the ankle in the corrective orthopedic or least distressed position.

Minimal aggravation of the fasciae typically occurs when the user's ankle 62 is maintained in the slight dorsiflexion position. Eliminating most, if not all, aggravation of the fasciae helps reduce inflammation to the fasciae and therefore, promote healing of plantar fascitis.

After placing the adhesive bandage 10 onto the user's foot 60 when the ankle 62 is in the slight dorsiflexion position, the proximal end 12 of the adhesive bandage 10 may be adhered to, or affixed diagonally over a distal and medial end 66 of a tibia bone 68 while the distal end 14 of the adhesive bandage 10 may be adhered to, or affixed over a base 70 of a $5^{th}$ metatarsal 72. The adhesive bandage 10 that is used to treat plantar fascitis is preferably non-sterile and long enough to span a diagonal length between the distal and medial end 66 of the tibia bone 68 and the base 70 of the $5^{th}$ metatarsal 72. Preferably, the proximal end 12 of the adhesive bandage 10 is adhered diagonally to a location slightly beyond the distal and medial end 66 of the tibia bone 68 while the distal end 14 of the adhesive bandage 10 is adhered diagonally to a location slightly beyond the base 70 of the $5^{th}$ metatarsal 72.

When the user's foot 60 and/or ankle 62 deviates from the slight dorsiflexion position, one or more cutaneous nerves (not shown) in the foot are stimulated, and one or more pain signals are consequently communicated to the user. For example, when the ankle 62 or foot 60 are in plantar flexion, plantar flexion/supination or plantar flexion/supination/inversion position, the adhesive bandage 10 located on the ankle 62 and/or foot 60 stretches.

As a result, the cutaneous sensory nerves (not shown) that are located in the user's foot 60 are stimulated or activated by the stretch, and pain signals are transmitted to the central nervous system of the user through afferent pain neuroreceptors (nociceptors). After transmission, the pain signals are integrated in the central nervous system and subsequently communicated to the user. Therefore, stimulation of the cutaneous sensory nerves with transmission of pain signals through the central nervous system to the user induces the somatic sensation reflex arc located in the user's foot 60.

After the pain signals are received by the user, the user must make a decision to respond to the pain signals by (1) continuing to maintain the foot 60 and/or ankle 62 in plantar flexion, plantar flexion/supination or plantar flexion/supination/inversion position, or (2) eliminating the pain by returning the foot 60 and/or ankle 62 to the slight dorsiflexion position. When the user chooses to eliminate the pain, the user relieves the stretch on the adhesive bandage 10 by returning the ankle 62 to the slight dorsiflexion position. Therefore, the adhesive bandage 10 dynamically maintains the corrective orthopedic position of the ankle 62 by providing an immediate cutaneous stimulus to the user any time the ankle 62 deviates from the slight dorsiflexion position.

In addition, the adhesive bandage 10 is a dynamic method of treatment that still permits full range of motion of the ankle 62 without compromising ankle 62 function. Thus, the dynamic quality of the adhesive bandage 10 enables the user to perform work activities or maintain natural resting positions ankle 62 for brief periods of time, while subsequent and continuous cutaneous stimulation reminds the user to return the ankle 62 to the corrective orthopedic position.

The adhesive bandage 10 also restricts movement of the foot 60 and/or ankle 62 by stimulating cutaneous sensory nerves located under the adhesive bandage 10 that signal the user to keep the ankle 62 in the slight dorsiflexion position. Furthermore, the adhesive bandage 10 reminds the user to retain the ankle 62 and/or foot 60 in the corrective orthopedic position so that most, if not all aggravation to the fasciae (not shown) is eliminated during various manual activities.

Similarly, the adhesive bandage 10 of the present invention provides a unique approach to the conservative treatment of plantar fascitis. Likewise, using the adhesive bandage 10 to treat plantar fascitis in accordance with the present invention eliminates cumbersome and awkward use of other devices and/or apparatuses like night splints that decrease user compliance and hinder volitional correction of the disorder of the ankle and/or foot. Furthermore, the adhesive bandage 10 does not compromise the cosmetic appearance of the user's foot 60 and/or ankle 62 while undergoing treatment for plantar fascitis.

Figure 9:
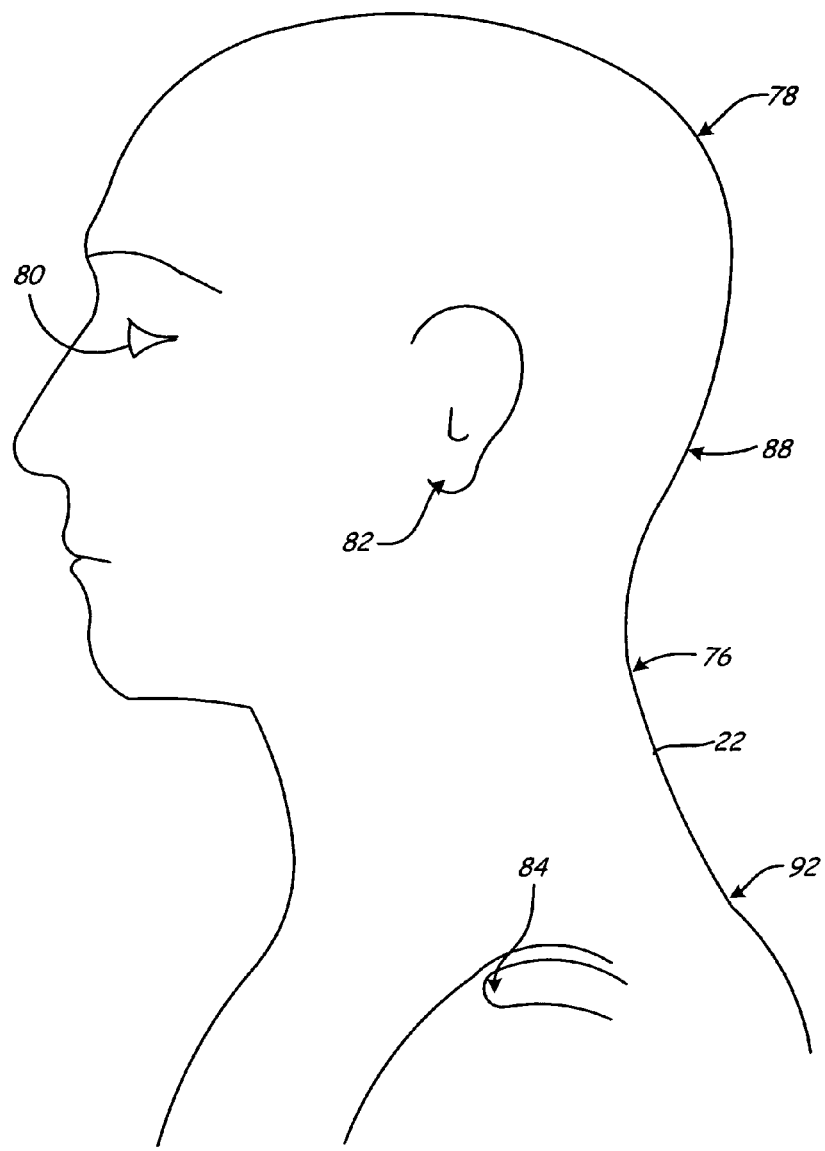
FIG. 9 is a lateral view of a user's neck that is placed in a correct orthopedic position.

The adhesive bandage of the present invention may also be applied to treat neck pain and/or disorders. When the adhesive bandage 10 is used to treat neck pain and/or disorder, the adhesive bandage 10 is placed onto the dorsal cutaneous surface 22 of a user's neck 76 when the user's neck 76 and head 78 are positioned in slight extension. In the slight extension position, a user's eyes 80 are focused straight ahead while an ear 82 is positioned in vertical alignment with respect to acromion 84, as best illustrated in FIG. 9.

Figure 10:
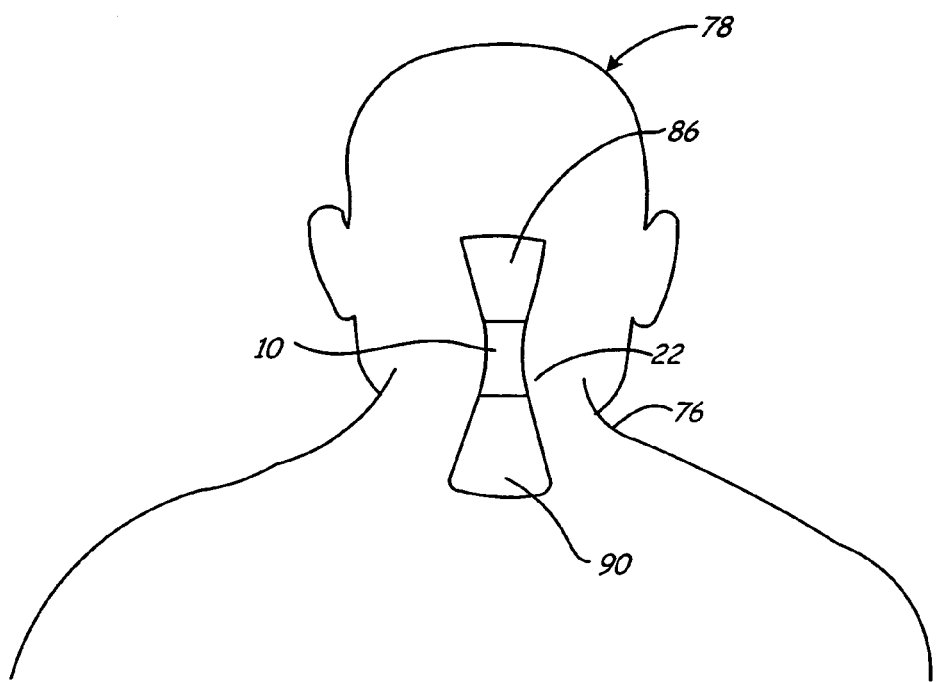
FIG. 10 is a posterior view of the adhesive bandage of the present invention applied to the user's neck depicted in FIG. 9.

After placing the adhesive bandage 10 onto the user's neck 76 when the neck 76 is in slight extension or the corrective orthopedic position, a cephalic end 86 of the adhesive bandage 10 may be adhered to, or affixed over a sub-occipital region 88 of the user's head 78 while a caudal end 90 may be adhered to, or affixed over a $7^{th}$ cervical vertebra spinous process 92 as best depicted in FIG. 10. The adhesive bandage 10 that is used to treat neck pain and/or disorder is preferably long enough to span a vertical length between the sub-occipital region 86 of the user's head 78 and the $7^{th}$ cervical vertebra spinous process 92. Preferably, the cephalic end 86 is adhered vertically to the user's neck 76 at a location slightly beyond the sub-occipital region 88 of the user's head 78 while the caudal end 90 is adhered vertically at a location slightly beyond the $7^{th}$ cervical vertebra spinous process 92.

When the user's neck 76 deviates from slight extension position or corrective orthopedic position, one or more cutaneous nerve(s) (not shown) in the user's neck 76 are stimulated, and one or more pain signal(s) are communicated to the user. For example, when the neck 76 or head 78 is in flexion or reverse lordosis, the adhesive bandage 10 stretches. Cutaneous sensory nerves (not shown) that are located in the user's neck 76 are stimulated or activated by the stretch, and pain signals are transmitted to the Central Nervous System of the user through afferent pain neuroreceptors (nociceptors). After transmission, the pain signals are integrated in the Central Nervous System and subsequently communicated to the user. Stimulation of the cutaneous sensory nerves with transmission of pain signals through the Central Nervous System to the user induces the somatic sensation reflex arc located in the user's neck 76.

After the pain signals are received by the user, the user must make a decision to respond to the pain signals by (1) continuing to maintain the neck 76 in the flexion or reverse lordosis position, or (2) eliminating the pain by returning the neck 76 to the corrective orthopedic position. Therefore, the adhesive bandage 10 dynamically maintains the corrective orthopedic position of the neck 76 by providing an immediate cutaneous stimulus to the user any time the neck 76 deviates from the corrective orthopedic position.

In addition, the adhesive bandage 10 permits full range of motion of the neck 76 without compromising neck 76 function. Thus, the dynamic quality of the adhesive bandage 10 enables the user to perform work activities or maintain the neck 76 for brief periods of time, while subsequent and continuous cutaneous stimulation reminds the user to return the neck 76 to the corrective orthopedic position. The adhesive bandage 10 restricts movement of the neck 76 by stimulating cutaneous sensory nerves of the user's neck 76 under the adhesive bandage 10 that signal the user to keep the neck 76 in the least distressed neck position.

The adhesive bandage 10 of the present invention provides an innovative approach to the conservative treatment of neck pain or disorder. Additionally, using the adhesive bandage 10 to treat neck pain or disorder in accordance with the present invention eliminates cumbersome and awkward use of other devices and/or apparatuses, and permits unrestricted use of the user's neck 76 if required. Furthermore, the adhesive bandage 10 does not compromise the cosmetic appearance of the user's neck 76 while undergoing treatment for neck pain or disorder.

Figure 11:
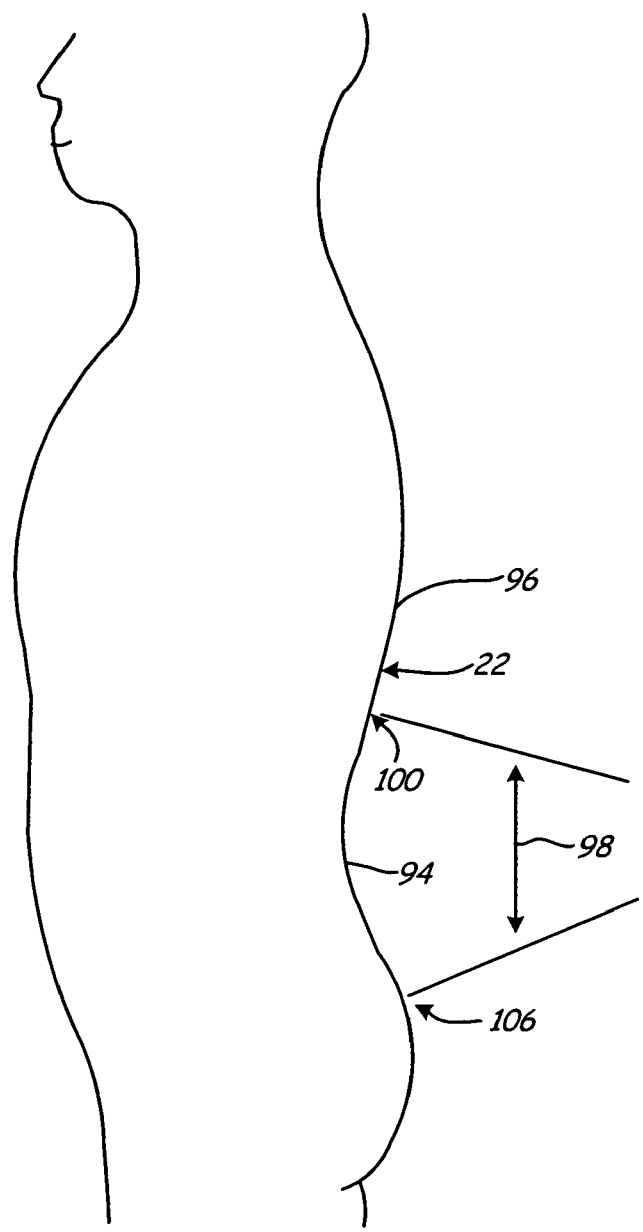
FIG. 11 is a lateral view of a user's back that is placed in the correct orthopedic position.

The adhesive bandage of the present invention may also be applied to treat back pain and/or disorders. When the adhesive bandage 10 is used to treat back pain and/or disorder, the adhesive bandage 10 is placed onto a lumbar region 94 of a user's back 96 when the user's back 96 is placed in slight extension position or a proper lordodic posture 98 as the user stands in an upright position, as best illustrated in FIG. 11.

Figure 12:
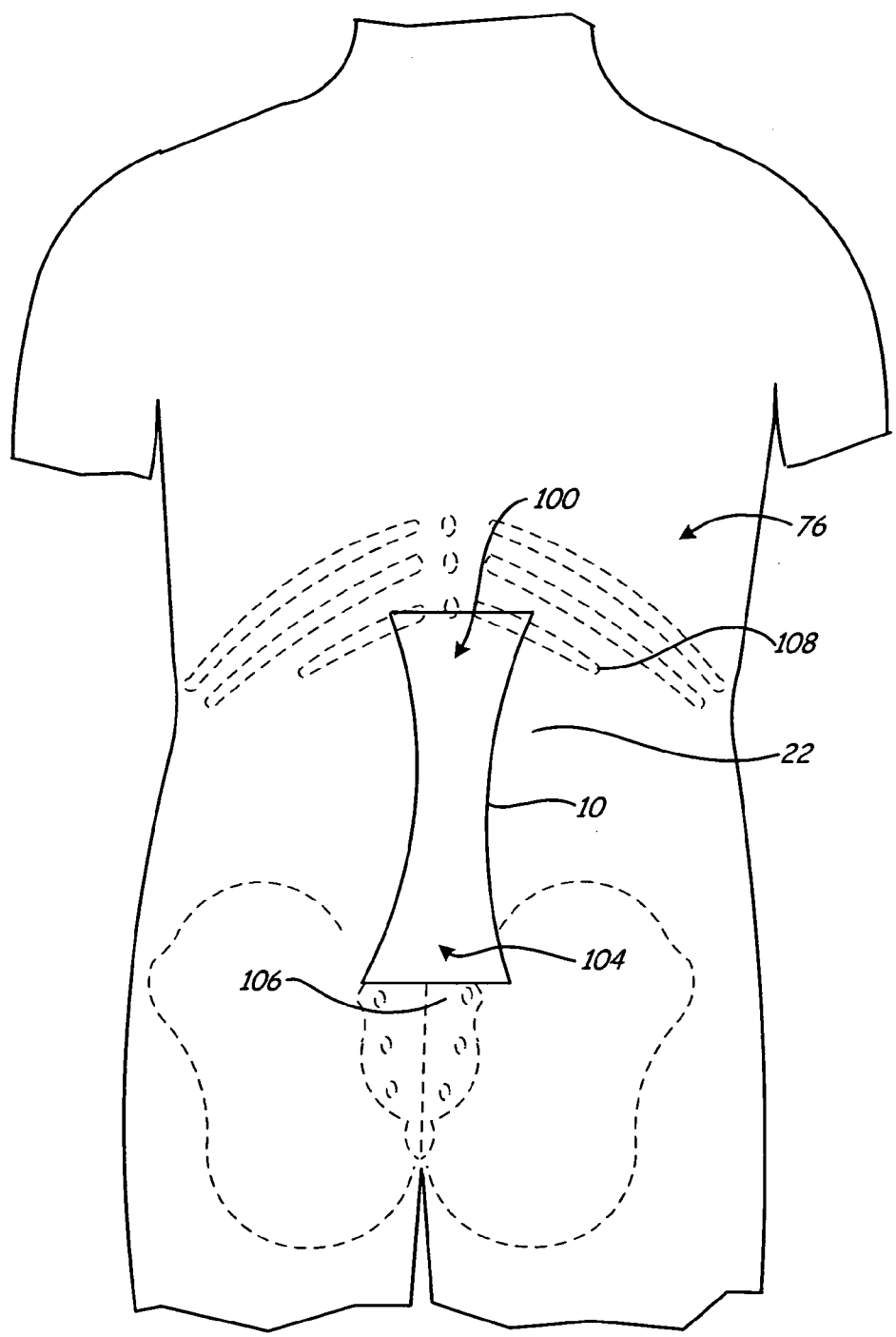
FIG. 12 is a posterior view of the adhesive bandage of the present invention applied to the user's back depicted in FIG. 11.

After placing the adhesive bandage 10 onto the user's back 96 when the back 96 is in the slight extension position 98, a cephalic end 100 of the adhesive bandage 10 may be centrally adhered to, or centrally affixed over a lower thoracic (upper lumbar) area (not shown) and a caudal end 104 of the adhesive bandage 10 is centrally affixed to a sacral base 106, as best depicted in FIG. 12. The adhesive bandage 10 that is used to treat back pain and/or disorder is preferably long enough to span a vertical length between the sacral base 106 and a $1^{st}$ lumbar vertebra 108. Preferably, the cephalic end 100 is adhered vertically to the user's back 96 at a location slightly beyond the $1^{st}$ lumber vertebra 108 of the user's back 96 while the caudal end 104 is adhered vertically at a location slightly beyond the sacral base 106.

When the user's back 96 deviates from the proper lordodic posture 98, one or more cutaneous nerve(s) (not shown) in the user's back 96 are typically stimulated, and one or more pain signal(s) are communicated to the user. For example, when the back 96 is in flexion or reverse lordosis, the adhesive bandage 10 stretches. Cutaneous sensory nerves (not shown) that are located in the user's back 96 are stimulated or activated by the stretch, and pain signals are transmitted to the Central Nervous System of the user through afferent pain neuroreceptors (nociceptors). After transmission, the pain signals are integrated in the Central Nervous System and subsequently communicated to the user. Stimulation of the cutaneous sensory nerves with transmission of pain signals through the Central Nervous System to the user induces the somatic sensation reflex arc located in the user's back 96.

After the pain signals are received by the user, the user must make a decision to respond to the pain signals by (1) continuing to maintain the back 96 in the flexion or reverse lordosis position, or (2) eliminating the pain by returning the back 96 to the proper lordodic posture 98. Therefore, the adhesive bandage 10 dynamically maintains the proper lordodic posture of the back 96 by providing an immediate cutaneous stimulus to the user any time the back 96 deviates from the proper lordodic posture 98.

In addition, the adhesive bandage 10 permits full range of motion of the back 96 without compromising back 96 function. Thus, the dynamic quality of the adhesive bandage 10 enables the user to perform work activities for brief periods of time, while subsequent and continuous cutaneous stimulation reminds the user to return the back 96 to the corrective orthopedic or proper lordodic posture 98. The adhesive bandage 10 restricts movement of the back 96 by stimulating cutaneous sensory nerves of the user's back 96 under the adhesive bandage 10 that signal the user to keep the back 96 in the proper lordodic posture 98.

The adhesive bandage 10 of the present invention provides an innovative approach to the conservative treatment of back pain and/or disorder. Additionally, using the adhesive bandage 10 to treat back pain or disorder in accordance with the present invention eliminates cumbersome and awkward use of other devices and/or apparatuses, and permits unrestricted use of the user's back 96 if required. Furthermore, the adhesive bandage 10 does not compromise the cosmetic appearance of the user's back 96 while undergoing treatment for back pain or disorder.

Utilization of the adhesive bandage in accordance with the present invention is rehabilitative, and capable of being applied to all disorders where repetitive strain injuries may exist. Furthermore, the adhesive bandage is effective in providing relief in both acute and chronic cases of disorders associated with the skeletal system and associated part of the skeletal system like disorders of the wrist, foot, neck and back. The adhesive bandage therefore, provides a means for non-invasive relief from the pains associated with pain and/or disorders of the skeletal system and associated parts of the skeletal system while permitting only necessary movement of treated regions.

Another unique feature of the present invention is an ability of the adhesive bandage 10 to operate as a protective and corrective apparatus in order to prevent future injuries from occurring. For example, the adhesive bandage 10 may prevent the user from improperly positioning the hand and/or wrist, for example, during performance of a particular task to avoid injury to the carpal tunnel. Thus, the present invention may operate as a training apparatus that prohibits the user from placing their wrist in an improper position while providing positive reinforcement for the correct positioning during the particular task. Therefore, after a period of time, the user will be trained in the proper placement of the wrist for the task.

Utilization of adhesive bandages, such as BAND-AID® are also quite common within the United States, and adhesive bandages typically provide comfort and emotional relief of pain and injury to the user. Thus, utilization of the adhesive bandage in accordance with the present invention also provides emotional relief of pain to the user and helps promote healing.

Although the present invention has been described with reference to preferred embodiments, workers skilled in the art will recognize that changes may be made in form and detail without departing from the spirit and scope of the invention.

The invention claimed is:

1. A method of treating carpal tunnel syndrome, the method comprising:
   placing a user's wrist in a corrective orthopedic position;
   adhering an adhesive bandage onto the user's wrist in the corrective orthopedic position, wherein the adhesive bandage extends diagonally from a lateral end of a radius bone to a $5^{th}$ metacarpal bone on a top side of the wrist, and wherein the adhesive bandage is effective to stimulate a cutaneous sensory nerve when the wrist deviates from the corrective orthopedic position; and
   returning the wrist to the corrective orthopedic position after stimulating the cutaneous sensory nerve.

2. The method of claim 1 wherein the adhesive bandage is adhered to the lateral radius bone and the $5^{th}$ metacarpal bone when the user's wrist is in the corrective orthopedic position.

3. The method of claim 1 wherein the adhesive bandage is effective to remind the user to keep the wrist in the corrective orthopedic position.

\* \* \* \* \*